(12) United States Patent
Schermeier et al.

(10) Patent No.: US 9,089,664 B2
(45) Date of Patent: Jul. 28, 2015

(54) MEDICAL DEVICE WITH A FLUID PORT

(75) Inventors: Olaf Schermeier, Lübeck (DE); Gerd Wotha, Warnstorf (DE); Markus Steeger, Lübeck (DE); Ludger Tappehorn, Stockelsdorf (DE)

(73) Assignee: Dräger Medical GmbH, Lübeck (DE)

( * ) Notice: Subject to any disclaimer, the term of this patent is extended or adjusted under 35 U.S.C. 154(b) by 2323 days.

(21) Appl. No.: 11/924,729

(22) Filed: Oct. 26, 2007

(65) Prior Publication Data
US 2008/0173308 A1    Jul. 24, 2008

(30) Foreign Application Priority Data
Jan. 24, 2007  (DE) .......................... 10 2007 003 594

(51) Int. Cl.
*A61M 16/08*   (2006.01)
*A61M 39/10*   (2006.01)
*G06K 7/10*    (2006.01)

(52) U.S. Cl.
CPC ........... *A61M 16/08* (2013.01); *A61M 39/1055* (2013.01); *G06K 7/10178* (2013.01); *A61M 16/0816* (2013.01); *A61M 2205/14* (2013.01); *A61M 2205/3569* (2013.01); *A61M 2205/3592* (2013.01); *A61M 2205/6054* (2013.01)

(58) Field of Classification Search
CPC . A61M 16/00; A61M 16/08; A61M 16/0816; A61M 16/0875; A61M 2205/14; A61M 2205/3546; A61M 2205/3569; A61M 2205/3576; A61M 2205/3592; A61M 2205/6054; G06K 7/10178; G06K 19/0723; F04B 49/065; A61B 1/00016; A61B 1/00029; A61B 1/00119; A61B 1/00128

USPC ............ 128/200.24, 205.25, 206.12, 206.27, 128/206.28; 600/529–542; 343/895; 235/491–493; 455/41.1

See application file for complete search history.

(56) References Cited

U.S. PATENT DOCUMENTS

| | | | |
|---|---|---|---|
| 5,910,776 A | 6/1999 | Black | |
| 7,004,168 B2 * | 2/2006 | Mace et al. | 128/206.21 |
| 7,642,916 B2 * | 1/2010 | Phipps et al. | 340/572.7 |
| 7,701,346 B2 * | 4/2010 | Lindsay et al. | 340/572.3 |
| 2004/0127937 A1 * | 7/2004 | Newton | 606/202 |
| 2006/0066498 A1 * | 3/2006 | Abe et al. | 343/788 |
| 2006/0096597 A1 * | 5/2006 | Amann | 128/205.27 |
| 2007/0222603 A1 | 9/2007 | Lai et al. | |

FOREIGN PATENT DOCUMENTS

| | | |
|---|---|---|
| EP | 1 731 089 A1 | 12/2006 |
| WO | 2006/134428 A1 | 12/2006 |

* cited by examiner

*Primary Examiner* — Alireza Nia
*Assistant Examiner* — Raymond E Harris
(74) *Attorney, Agent, or Firm* — McGlew and Tuttle, P.C.

(57) ABSTRACT

A medical device has a fluid port (2), a tube (20), a socket (4), which can be connected to the fluid port and to the tube with freely selectable rotation positions. The tube is provided with a transponder (22) and with a writing and reading device for communication with the transponder, which has an antenna (24) in the area of the fluid port. The socket is provided with a coil (5, 6) each, whose axis of rotation is directed essentially coaxially to the axis of rotation about which the relative rotation position of the socket is variable. The two coils are connected by electric lines (8), to which at least one capacitor (9) is connected as a circuit component. The coils, the electric lines and the circuit component form an electric oscillatory circuit for transmitting signals between the writing and reading device and the transponder.

22 Claims, 2 Drawing Sheets

MEDICAL DEVICE WITH A FLUID PORT

CROSS REFERENCE TO RELATED APPLICATIONS

This application claims the benefit of priority under 35 U.S.C. §119 of German Patent Application DE 10 2007 003 594.4 filed Jan. 24, 2007, the entire contents of which are incorporated herein by reference.

FIELD OF THE INVENTION

The present invention pertains to a medical device with a fluid port, a tube, a socket, which can be connected to the fluid port, on the one hand, and to the tube, on the other hand, with a freely selectable rotation position at each, in order to establish a fluid connection between the fluid port and the tube, wherein the tube is provided with a transponder at its end at which it is connected to the socket, and with a writing and reading device for communication with the transponder, which has an antenna in the area of the fluid port.

BACKGROUND OF THE INVENTION

A typical example of such a medical device is a respirator (also known as a ventilator), at the breathing gas connection of which a tube can be connected via a socket, which said tube leads into the respiration circuit. At their ends facing the respirator, such tubes are provided with transponders, which make it possible for the respirator with an associated writing and reading device to exchange information with the transponder and to make available as a result information on the type and other properties of the connected tube. The antenna of the writing and reading device is located close to the breathing gas connection of the respirator; the antenna can surround this breathing gas connection, for example, concentrically.

One problem of such devices is that a certain distance between the antenna at the fluid port and the transponder at the tube is inevitable, because the socket is located between the tube and the fluid port. Since the range of radio frequency signals, which are exchanged between the antenna of the writing and reading device and that of the transponder, is limited, problems may arise in signal transmission. Another problem is that the connections of the socket to the fluid port, on the one hand, and to the tube, on the other hand, do not predetermine a fixed or predetermined rotation position of the fluid port and the socket, on the one hand, and the socket and the tube, on the other hand, i.e., the connections may take place, in principle, in any relative rotation position of the components in relation to one another, i.e., both the rotation position of the socket in relation to the fluid port and the relative rotation position of the socket in relation to the tube may vary over a relative angle of rotation of 360°. The position which the antenna of the transponder will assume relative to the antenna of the writing and reading device is unpredictable due to these circumstances.

Furthermore, the rotatable connection of the fluid port or the tube to the socket rules out an electrically conductive connection from practical points of view, because such a connection could be embodied only at a considerable design effort, for example, with sliding contacts.

SUMMARY OF THE INVENTION

The object of the present invention is to improve a medical device with a tube connection via a socket such that high reliability of signal transmission is guaranteed between the writing and reading device of the medical device and the transponder at the tube.

Provisions are made according to the present invention for the socket to be provided with a coil each in the areas of its respective connection ends, the axis of the respective coil being essentially coaxial to the axis of rotation about which the relative rotation position of the socket in relation to the fluid port or to the tube is variable. The coils are connected to one another via an electric line, a capacitor being connected as an additional circuit component to the line and to the coils in order to form an electric oscillatory circuit for the transmission of signals between the writing and reading device and the transponder. The electric oscillatory circuit forms an inductive bridging element, which bridges over a large part of the section between the antenna of the writing and reading device and that of the transponder, which offers a substantial improvement of signal transmission compared to a pure radio frequency radio transmission. Moreover, it is ensured by the rotationally symmetrical arrangement of the coils in the area of the connection ends of the socket that an essentially rotationally symmetrical field is generated, so that the signal transmission is independent from the relative rotation position of the socket in relation to the fluid port, on the one hand, and to the tube, on the other hand. The coil comprises at least one winding of a wire, whose central axis coincides with the axis of rotation about which the rotation position of the connection of the socket to the fluid port or to the tube is variable. The coil may have a plurality of windings, which extend in the form of a spiral line with an axis coinciding with the axis of rotation. As an alternative, the coil may also have the shape of a spiral, whose center is located on the axis of rotation and which extends in a plane extending at right angles to the axis of rotation.

The coils act here both as antennas and as inductive elements of the oscillatory circuit. The radio frequency and the width of the resonance curve can be preset in a suitable manner by appropriately selecting the capacity of the connected capacitor and optionally the impedance of a connected resistor, so that they are tuned to the transmission and reception frequency distribution of the writing and reading device and of the transponder.

The coil located at the end of the socket at which the socket is connected to the fluid port receives a radio frequency signal, which is emitted by the antenna of the writing and reading device and which reaches the coil located at the other connection end via the oscillatory circuit, which in turn leads there to the emission of a corresponding radio frequency signal, which will be received by the antenna of the transponder. Conversely, a radio frequency signal emitted by the antenna of the transponder reaches the coil located at the fluid port-side end of the socket via the oscillatory circuit and causes the emission of a corresponding radio frequency signal, which will be received by the antenna of the writing and reading device.

Provisions may be made for introducing a core consisting of a ferromagnetic material into the interior space of at least one coil in order to bring about focusing of the coil field. This may be a separate component. As an alternative, the socket or parts thereof may be made of a ferromagnetic material.

The present invention will be described below on the basis of exemplary embodiments in the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
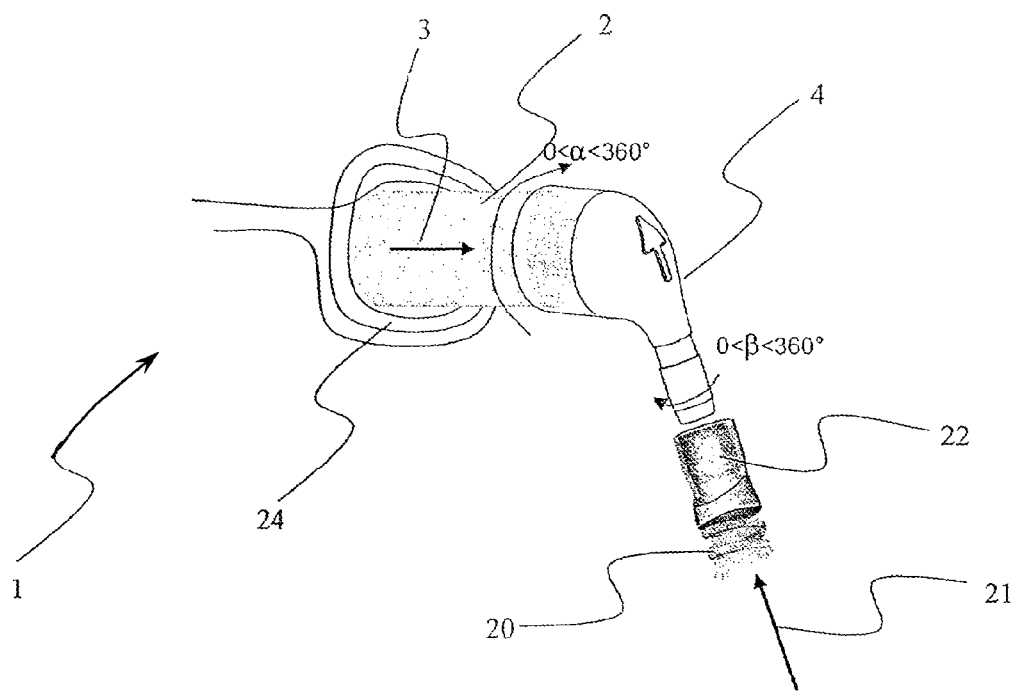
FIG. 1 is a schematic view of a respirator with a tube connected thereto via a socket.

Referring to the drawings in particular, FIG. 1 shows a schematic partial view of a medical device, namely, a medical respirator, wherein the respirator proper is designated by reference number 1. A socket 4 can be connected to the fluid port 2 of the respirator 1. The connection is brought about by means of a plug-type connection, so that the relative rotation position α of the fluid port 2 and the socket 4 in relation to one another is completely variable: α=0-360° (the rotational position is freely selectable about a first end axis). The tube 20 can likewise be connected to the opposite end of the socket 4 by means of a plug-type connection, so that the relative angle of rotation β between the tube 20 and the socket 4 is also completely variable (the rotational position is freely selectable about a second end axis). The tube 20 is provided, at its connection end near the socket 4 (near the second connection end of socket 4), with an RFID (Radio Frequency Identification) transponder 22, in which information on the type and other properties of the tube 20 can be stored.

This information is read by a writing and reading device associated with the respirator 1. The device has an antenna 24, which is arranged such that it surrounds the fluid port 2. The RFID transponder 22 at the tube responds to a polling signal of the writing and reading device, which is emitted via the antenna 24, with response signals, which are finally received, in turn, by the antenna 24 of the writing and reading device.

Figure 2:
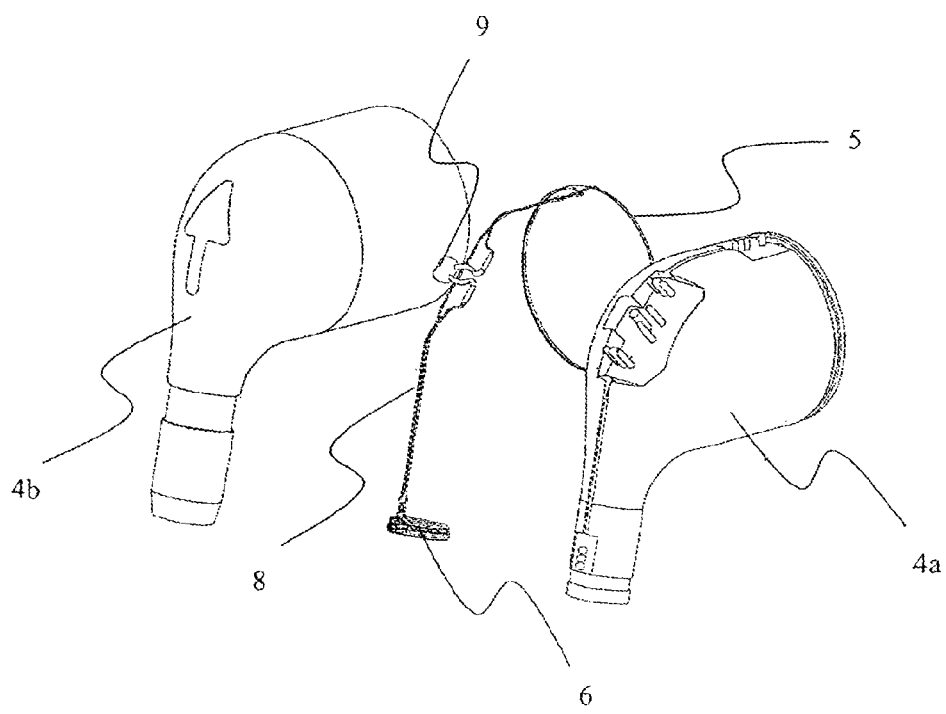
FIG. 2 is a schematic view of the components that are used to build up a socket to be used in connection with the present invention.

To guarantee the reliability of data transmission between the antenna 24 of the writing and reading device and the transponder 22 despite the distance caused by the socket 4 and despite the variable rotation positions α and β of the socket 4 in relation to the respective connection parts, provisions are made for arranging a coil each in the area of each connection end of the socket 4, these coils being designated by the reference numbers 5 and 6 in FIG. 2. The coils are connected to one another by at least one electric line 8, and a capacitor 9 is, furthermore, connected as another circuit component. The electric properties of the coils 5, 6, the line 8 and the capacitor 9 are selected to be such that the resonance frequency of the oscillatory circuit formed is tuned to the transmission and reception frequency of the writing and reading device and of the transponder 22.

Each coil 5, 6 is arranged in the corresponding connection end of the socket 4 such that its axis coincides with the axis of rotation (a first end axis or second end axis) about which the relative rotation position of the respective connection end of the socket is variable. The first end axis about which the rotation position of the connection of the socket 4 relative to the fluid port 2 is variable is schematically indicated by arrow 3. The second end axis about which the relative rotation position of the tube in relation to the opposite end of the socket 4 is variable is correspondingly indicated by arrow 21.

Due to the rotationally symmetrical design of the coils 5, 6 in relation to the respective connection of the socket 4, transmission that is independent from the rotation position of the socket 4 in relation to the fluid port 2 and to the tube 20 is ensured. Furthermore, substantially better signal transmission is achieved due to the signal guiding via the oscillatory circuit 5, 6, 8, 9 compared to a pure radio frequency radio transmission.

FIG. 2 shows a first embodiment of a socket to be used in connection with the present invention, wherein a first inner wall part 4a is present, which is provided at the respective connection ends with recessed areas, in which the coils 5, 6 are accommodated. The coils 6 and 5 are wound from wire, which passes over into the line 8, which is designed as a wire line and in which at least one capacitor 9 is connected as a circuit component between the coils. After mounting the oscillatory circuit 5, 6, 8, 9 on the inner part 4a of the socket 4, a second, outer housing part 4b can be pushed over, so that the oscillatory circuit is embedded between the inner and outer walls of the socket 4. This embedding in the housing is advantageous because the socket 4 will then be able to be cleaned and disinfected in the usual manner.

Figure 3:
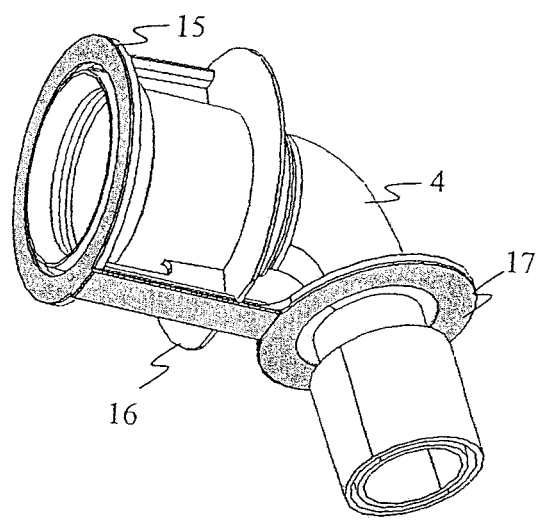
FIG. 3 is a perspective view of a socket to be used in connection with the present invention.

FIG. 3 shows an alternative embodiment of a socket 4 to be used with the present invention. The housing part of the socket 4 is provided in this case with annular surfaces 15 and 17, the ring plane always being directed at right angles to the axis of rotation about which the connection of the socket 4 with its connection part is variable. In other words, the planes of the annular bodies 15, 17 are essentially parallel to the plane of the corresponding connection opening of the socket 4. As is shown by the example of the annular surface 17, this annular body may have a certain distance from the plane of the connection opening.

The two annular surfaces 15, 17 are connected to one another by a web 16. Furthermore, a flexible printed circuit board is provided, which has two annular areas corresponding to the annular surfaces 15 and 17, which are connected to one another by a web-like area corresponding to the web 16. The coils 5 and 6 (not shown in FIG. 3) are placed on this flexible printed circuit board in the annular areas, the electric connection line and the capacitor being accommodated on the web-like part of the printed circuit board, which comes into contact with the web 16. The flexible printed circuit board may be provided with adhesive on one side in order to thus make it possible to bond the flexible printed circuit to the annular surfaces 15, 17 and to the web 16 located between them.

The coil to be arranged on the annular body 15 may be designed in this exemplary embodiment, for example, in the spiral form with a plurality of windings over the surface of the annular body 15.

While specific embodiments of the invention have been shown and described in detail to illustrate the application of the principles of the invention, it will be understood that the invention may be embodied otherwise without departing from such principles.

What is claimed is:

1. A medical device comprising:
   a fluid port;
   a tube;
   a socket part having a socket part first connection end for connection to said fluid port with freely selectable socket part rotation positions about a socket part first end axis and having a socket part second connection end for connection to said tube with freely selectable socket part rotation positions about a socket part second end axis to establish a fluid connection between said fluid port and said tube;

a transponder provided at an end of said tube at which said tube is connected to said socket;

a writing and reading device for communication with said transponder, said writing and reading device having an antenna in an area of said fluid port;

a first coil fixed to said socket and disposed rotationally symmetrical in an area of said first connection end essentially coaxial to said first end axis;

a second coil fixed to said socket and disposed rotationally symmetrical in an area of said second connection end essentially coaxial to said second end axis;

an electric line connecting said first coil and said second coil;

a capacitor connected to said electric line as a circuit component, wherein said first coil, said second coil, said electric line and said circuit component form an electric oscillatory circuit for transmitting signals from the writing and reading device to said transponder and vice versa independently from a relative rotational position of the socket in the fluid port and also independently from a relative rotational position of the socket relative to the tube.

2. A medical device in accordance with claim 1, wherein:
windings of said first coil extend around a flow channel of said socket in an area of a first connection opening of said first connection end; and
windings of said second coil extend around the flow channel of said socket in an area of a second connection opening of said second connection end.

3. A medical device in accordance with claim 2, wherein:
windings of said first coil are embedded in a wall portion of said socket adjacent to said first connection opening; and
windings of said second coil are embedded in a wall portion of said socket adjacent to said second connection opening.

4. A medical device in accordance with claim 3, wherein said electric line and said circuit component of said oscillatory circuit are embedded in the wall of said socket.

5. A medical device in accordance with claim 1, further comprising:
a first annular surface arranged at said socket first connection end, said first annular surface extending concentrically around an outer wall of said socket;
a second annular surface arranged at said socket second connection end, said second annular surface extending concentrically around the outer wall of said socket; and
a flexible printed circuit board, said coils, said electric line and said circuit component of the oscillatory circuit being arranged on said flexible printed circuit board, said flexible printed circuit board being bonded to said annular surfaces and to a web, whereby each of said coils lies on one of the respective annular surfaces.

6. A medical device in accordance with claim 5, wherein said annular surfaces and said web are injection-molded from a plastic in one piece with said socket.

7. A medical device in accordance with claim 1, further comprising a core of a ferromagnetic material, said core being disposed in an interior space of at least one of said coils to bring about a focusing of a coil field.

8. A medical device in accordance with claim 1, wherein:
the first coil comprises at least one winding of a first coil wire, the at least one winding of the first coil wire having a central axis that coincides with said first end axis; and
the second coil comprises at least one winding of a second coil wire, the at least one winding of the second coil wire having a central axis that coincides with said second end axis.

9. A medical device comprising:
a device fluid port with one of a male and female connection interface;
a tube for carrying fluid to or from the device fluid port, the tube having one of a male and female connection interface;
a socket connector with a wall structure defining a first connection end with one of a male and female connection interface cooperating with said device fluid port connection interface and forming an axial connection between said socket connector and said device fluid port with a freely selectable rotation position of said socket about a port axis and defining a second connection end with one of a male and female connection interface cooperating with said tube connection interface and forming an axial connection between said socket connector and said tube with a freely selectable rotation position of said socket about a tube axis, said socket connector establishing a fluid connection between said fluid port and said tube;
a transponder provided at a socket end of said tube;
a writing and reading device for communication with said transponder, said writing and reading device having an antenna in an area of said device fluid port;
a first coil supported by said socket connector in an area of said first connection end with said first coil extending rotationally symmetrical around a flow channel of said socket connector in the area of a first connection opening of said first connection end and essentially coaxial to said port axis with said socket connector connected to said device fluid port;
a second coil supported by said socket connector in an area of said second connection end with said second coil extending rotationally symmetrical around the flow channel of said socket connector in the area of a second connection opening of said second connection end and essentially coaxial to said tube axis with said socket connector connected to said tube;
an electric line connecting said first coil and said second coil;
a capacitor connected to said electric line as a circuit component, wherein said first coil, said second coil, said electric line and said circuit component form an electric oscillatory circuit for transmitting signals from the writing and reading device to said transponder and vice versa independently from a relative rotational position of the socket in the device fluid port and also independently from a relative rotational position of the socket relative to the tube.

10. A medical device in accordance with claim 9, wherein:
windings of said first coil extend around a flow channel of said socket connector in the area of said first connection opening of said first connection end; and
windings of said second coil extend around the flow channel of said socket connector in the area of said second connection opening of said second connection end.

11. A medical device in accordance with claim 10 wherein:
windings of said first coil are embedded in said wall structure of said socket connector, adjacent to said second connection opening; and
windings of said second coil are embedded in said wall structure of said socket connector, adjacent to said first connection opening.

12. A medical device in accordance with claim 9, further comprising:
- a first annular surface arranged at said first connection end of said socket connector said first annular surface extending concentrically around an outer wall of said socket connector;
- a second annular surface arranged at said second connection end of said socket connector said second annular surface extending concentrically around the outer wall of said socket connector; and
- a flexible printed circuit board, said coils, said electric line and said circuit component of the oscillatory circuit being arranged on said flexible printed circuit board, said flexible printed circuit board being bonded to said annular surfaces and to a web, whereby each of said coils lies on one of the respective annular surfaces.

13. A medical device in accordance with claim 12, wherein said annular surfaces and said web are injection-molded from a plastic in one piece with said socket connector.

14. A medical device in accordance with claim 9, wherein said electric line and said circuit component of said oscillatory circuit are embedded in said wall structure of said socket connector.

15. A medical device in accordance with claim 9, further comprising a core of a ferromagnetic material, said core being disposed in an interior space of at least one of said coils to bring about a focusing of a coil field.

16. A medical device comprising:
- a device fluid port;
- a tube for carrying fluid to or from the device fluid port;
- a socket connector with a wall structure defining a first connection end axially connecting said socket to said device fluid port with a freely selectable rotation position of said socket about a port axis and defining a second connection end axially connecting said socket to said tube with a freely selectable rotation position of said socket about a tube axis, said socket establishing a fluid connection between said fluid port and said tube;
- a transponder provided at a socket end of said tube;
- a writing and reading device for communication with said transponder, said writing and reading device having an antenna in an area of said device fluid port;
- a first coil supported by said socket in an area of said first connection end with a central axis that coincides with said port axis and essentially coaxial and rotationally symmetrical to said port axis with said socket connector connected to said device fluid port;
- a second coil supported by said socket in an area of said second connection end with a central axis that coincides with said tube axis and essentially coaxial and rotationally symmetrical to said tube axis with said socket connector connected to said tube;
- an electric line connecting said first coil and said second coil;
- a capacitor connected to said electric line as a circuit component, wherein said first coil, said second coil, said electric line and said circuit component form an electric oscillatory circuit for transmitting signals from the writing and reading device to said transponder and vice versa independently from a relative rotational position of the socket in the device fluid port and also independently from a relative rotational position of the socket relative to the tube, wherein a winding of said first coil extends around a flow channel of said socket in the area of a first connection opening of said first connection end and a winding of said second coil extends around the flow channel of said socket in the area of a second connection opening of said second connection end.

17. A medical device in accordance with claim 16, further comprising:
- a first annular surface arranged at said first connection end of said socket said first annular surface extending concentrically around an outer wall of said socket;
- a second annular surface arranged at said second connection end of said socket said second annular surface extending concentrically around the outer wall of said socket; and
- a flexible printed circuit board, said coils, said electric line and said circuit component of the oscillatory circuit being arranged on said flexible printed circuit board, said flexible printed circuit board being bonded to said annular surfaces and to a web, whereby each of said coils lies on one of the respective annular surfaces.

18. A medical device in accordance with claim 17, wherein said annular surfaces and said web are injection-molded from a plastic in one piece with said socket.

19. A medical device in accordance with claim 16 wherein:
- said winding of said first coil is embedded in said wall structure of said socket adjacent to said second connection opening; and
- said winding of said second coil is embedded in said wall structure of said socket adjacent to said first connection opening.

20. A medical device in accordance with claim 16, wherein said electric line and said circuit component of said oscillatory circuit are embedded in said wall structure of said socket.

21. A medical device in accordance with claim 16, further comprising a core of a ferromagnetic material, said core being disposed in an interior space of at least one of said coils to bring about a focusing of a coil field.

22. A socket part connectable to a fluid port of a medical device with a writing and reading device for communication with a transponder and having an antenna in an area of the fluid port and connectable to a tube carrying the transponder at an end of the tube, the socket part comprising:
- a socket part first connection end forming a freely rotatable axial connection to the fluid port wherein said freely rotatable axial connection to the fluid port holds the socket axially along a socket part first end axis relative to the fluid port and said freely rotatable axial connection to the fluid port allows the socket to freely rotate relative to the fluid port about said first end axis;
- a socket part second connection end forming a freely rotatable axial connection to the tube wherein said freely rotatable axial connection to the tube holds the socket axially along a socket part second end axis relative to the fluid port and said freely rotatable axial connection to the tube allows the socket to freely rotate relative to the tube about said second end axis;
- a first coil fixed to the socket part and disposed rotationally symmetrical in an area of said first connection end essentially coaxial to said first end axis;
- a second coil fixed to the socket part and disposed rotationally symmetrical in an area of said second connection end essentially coaxial to said second end axis;
- an electric line connecting said first coil and said second coil;
- a capacitor connected to said electric line as a circuit component, wherein said first coil, said second coil, said electric line and said circuit component form an electric oscillatory circuit for transmitting signals from the writing and reading device to said transponder and vice versa independently from a relative rotational position of the socket, in the fluid port, about said first end axis and also independently from a relative rotational position of the socket, relative to the tube, about said second end axis.

* * * * *